United States Patent [19]
Warnecke et al.

[11] Patent Number: 4,767,008
[45] Date of Patent: Aug. 30, 1988

[54] INJECTION MONITOR APPLIANCE

[76] Inventors: Armand E. Warnecke, 542 59th St., Downers Grove, Ill. 60516; Carl W. Metz, 803 S. 4th St., St. Charles, Ill. 60174

[21] Appl. No.: 115,342

[22] Filed: Nov. 2, 1987

[51] Int. Cl.$^4$ .......................................... B65D 85/20
[52] U.S. Cl. .................................. 206/570; 206/366; 206/370; 206/459; 206/514; 206/564; 220/326
[58] Field of Search ............... 206/223, 365, 366, 370, 206/372, 373, 459, 514, 564; 220/326

[56] References Cited

U.S. PATENT DOCUMENTS

| | | | |
|---|---|---|---|
| 1,907,187 | 5/1983 | Pierce | 206/803 |
| 2,740,516 | 4/1956 | Renn | 206/803 |
| 2,985,285 | 5/1961 | Riddle | 206/366 |
| 3,305,084 | 2/1967 | Higgins et al. | 206/366 |
| 3,777,882 | 12/1973 | McIntyre | 206/370 |
| 3,802,555 | 4/1974 | Grasty et al. | 206/370 |
| 4,250,998 | 2/1981 | Taylor | 206/570 |
| 4,266,669 | 5/1981 | Watson | 206/570 |
| 4,349,338 | 9/1982 | Heppler | 206/459 |
| 4,420,085 | 12/1983 | Wilson | 206/370 |
| 4,446,970 | 5/1984 | Fürther | 206/570 |

Primary Examiner—Jimmy G. Foster
Attorney, Agent, or Firm—Andrew F. Zikas

[57] ABSTRACT

The injection monitor kit appliance allows insulin or injection-dependent persons to maintain daily monitoring of injections taken and maintains a full week's supply of insulin, syringes and alcohol swabs in a convenient and portable container. The injection monitor kit is a secure and easily transportable container having assigned, separate slots for a select number of syringes, with the name of each day of the a calendar week located in relative proximity to each slot containing therein the syringes which should be administered that day. The appearance of a syringe in its slot indicates an injection not yet taken. Additionally, the appliance includes compartments for medication containers, alcohol swabs and a means for breaking off needles from spent syringes and storing such needles in a safe manner.

14 Claims, 3 Drawing Sheets

INJECTION MONITOR APPLIANCE

BACKGROUND OF INVENTION

The invention relates to means for monitoring the daily injection requirements of an insulin or injection-dependent person, and a means for facilitating tracking of injections taken or not taken, on a daily basis.

It is especially important for those persons taking a daily series of injections to keep an accurate count of those injections taken or not taken in order to allow the medication to produce the desired effect. It is very important for an insulin-dependent person to insure that he has taken his daily allotted number of shots. A person who is insulin-dependent needs an accurate scorecard. Making a mistake and either taking too much or too little—either of which is totally unacceptable—can be catastrophic. For a diabetic, duplication of a daily dose or doses of insulin can result in severe insulin shock which can cause brain damage or even death. Failure to administer one or more doses of insulin results in high blood sugar levels. This high blood sugar level causes condition called ketosis or acidosis. Ketones are organic acid compounds in the bloodstream. These acid compounds have a cumulative effect that will degrade vital body organs of an affected individual. A diabetic who misses a number of injections (say seven), stands a good chance of death. It is, therefore, extremely important to have a means of monitoring one's daily injections so as to enable a person to be secure that he has taken his injection, and has not taken more than he should.

There are prior art devices which are designed to hold only a few syringes and associated medications. Some are relatively large and cumbersome; some provide for containing a means of unnecessary, temporary, refrigeration of medication. Others are arranged to contain additional items which are needed only occasionally. Most importantly, much of what is available does not give an individual any way to monitor whether or not such person has taken a scheduled injection. Further, most prior art devices do not have the availability to monitor a full week of medication, such as provided by the invention. Additionally, some prior art kits are not adequately durable for sustained usage or are too cumbersome or are not large enough to contain everything needed for a full week of injections. Further, prior art devices or kits fail to provide a convenient means for securely disposing of spent syringes.

SUMMARY OF THE INVENTION

A primary object of this invention is to provide a simple and nearly foolproof means for permitting an insulin or injection-dependent person to keep track each day of the injections taken or not taken.

This invention provides an improved appliance allowing an injection-dependent person to safely and conveniently carry syringe assemblies, medication, alcohol swabs and needle disposing means in a very portable and durable device having a guide associated with a day of the week for a full week to keep track of those injections taken or not taken on a daily basis.

The invention is designed very simply so that it can be effective with a younger or an older person, or anyone who is easily confused. Further, the inventive device is durable, readily portable and easily transported to any job site or like public place in an average briefcase or the like.

To attain these and other objects and features of the invention, which will become more apparent from the following description, the invention provides an improved injection monitor appliance or kit which comprises a relatively safe, foolproof, light-weight, durable, portable and economical device adopted for use by injection-dependent individually to maintain a daily monitoring of injections taken.

The device or appliance of the invention comprises, in combination, a number of distinctive features or characteristics. One such feature comprises a relatively rigid container assembly having an upper and a lower closure member, with each respective member having bottom and side walls joined together to form a unit. The closure members are adapted to selectively mate with one another to define a hollow space therebetween selectively sealable from external environment. In certain embodiments, the closure members may be provided with a hinge means along adjacent side wall edges thereof so to enable the closure members to selectively pivot toward and away from each other, with a locking means, such as a snap-lock means, provided on adjacent side edge of the closure members, preferably opposite the hinge means. In presently preferred embodiments, at least the lower closure member is provided with a tray-receiving compartment therein.

Another feature of the invention comprises a semi-rigid tray, which is provided and adapted to securely fit within, for example, the lower closure member. The tray includes an upper wall plane which is substantially parallel with and abuts the bottom wall of the upper closure member when mated with the lower closure member so as to securely maintain any items within the tray in their respective position or location during any movement or jostling of the overall device.

Another feature of the invention comprises a plurality, preferably seven, one for each day of a calendar week (although other select chronological time units may be utilized) of parallely-disposed, horizontally-extending, open-topped elongated slots which are located or provided in a first area on the tray. Each of the slots has a depth dimension extending from the tray upper wall plane toward a lower wall plane thereof and adapted to contain a select number of syringe assemblies therein. The slots are, preferably, separated from each other by respective partition walls, with a finger-tip receiving open groove located at a midpoint area of each partition wall to enable a user to insert a finger tip in such open groove and readily lift a syringe assembly from a select slot. Yet another feature of the invention comprises a first indicia means which may be associated with each respective slot designating a select day of a week thereon to enable a user to quickly and accurately determine which slot (and syringe) is to be utilized on a given day.

Another feature of the invention comprises a plurality, preferably at least two (although any other number may be utilized), of medication container-receiving depressions which are located or provided at a second area of the tray, adjacent and spaced from the first area thereof. In certain embodiments of the invention, a second indicia means may be associated with each respective depression to designate the type of medication in the container within such depression.

Another feature of the invention comprises a recess which is located or provided at a third area of the tray, adjacent and spaced from the first and second areas thereof. The recess is adapted for snugly receiving a plurality, say fourteen or more, prewrapped alcohol swabs therein to enable a user to sterilize a select skin area and/or medication container openings before each injection.

Another feature of the invention comprises a well opening which is located or provided on the tray at a fourth area thereof, adjacent and spaced from the first, second and third areas for receiving syringe needles therein after such needles have been broken off from the remaining syringe assembly. Another feature of the invention comprises a cover member, preferably metallic, which is provided to frictionally fit within an upper peripheral area of the well opening. The cover member includes a syringe-needle receiving aperture in a central area thereof to receive syringe needles therein and aid in breaking off needles from spent syringe assemblies. In a presently preferred embodiment, the cover member is a stainless steel disc and is provided with an aperture having a through hole diameter ranging from about 0.75 to about 0.25 millimeters. In certain embodiments, the well opening may include a tool-receiving depression along an upper peripheral area of such opening for receiving a tool to be inserted beneath cover member for selective removal thereof.

In certain embodiments of the invention, the semirigid tray may be adhesively secured to the bottom wall of the lower closure member. The adhesive coating may be applied to select areas of the outwardly-facing bottom wall of the tray or the adhesive coating may be applied to lateral side edge walls of the tray for adhesion with supporting portions of the lower closure member. In other embodiments, the semirigid tray may be an integral portion of the lower closure member. Integration may be achieved through blow-molding or vacuum-forming techniques well known in the art.

In certain embodiments of the invention, a retaining means may be provided in working relation with each respective slot in the tray to securely maintain a select number of syringe assemblies within such slots and prevent the syringe assemblies from accidentally spilling or otherwise being removed from the slots. In one embodiment, the retaining means may comprise an elastomeric band extending across each respective slot, with the ends of such band being anchored along the outermost partition walls between the slots. In another embodiment, the retaining means may comprise deformable lips, preferably formed of a synthetic foam-like material, attached to respective side walls of each partition wall and extending toward one another across each respective slot. In yet another embodiment, the retaining means may comprise a snap-lock cap which frictionally fits between adjacent partition walls and across each respective slot.

The injection monitor kit or appliance of the invention is designed to be an easy and nearly foolproof means for tracking injections taken or not taken on a daily and weekly basis. The outside of the kit or appliance is a relatively unbreakable, box-like container, made of plastic or some other lightweight, durable material. This container may be made with any degree of clarity; it may also be made with a clear window in order to allow a user to quickly take account of the contents therein. The outer container is preferably smooth with no rough edges to catch or abrade, inside or out. A removable lid may be separate or hinged to the bottom unit of the device. In either instance, it is important that the lid fit closely against the top edge of the bottom unit of the kit or appliance so that there is no shifting of interior contents. It is especially important that syringes or syringe assemblies stored in predetermined positions within an interior tray are not accidentally moved or interchanged, thereby negating the means for tracking injections taken or not taken. The lid and bottom units should mate securely with one another so that there will be little chance for the container to open independently during transport or storage. This may be accomplished by special conformation of the lid to the bottom by providing a series of ridges or lips embossed into either unit to create a snap or pressure fit, or by using any one of a number of conventional latch closures. This combination then creates a total exterior package.

The inside of the kit may be created as a separate unit, or if desired as part of the bottom unit. A central area of this inner unit or tray is provided with a number (preferably seven) of separate finger-like slots. These slots are positioned side by side and are of a length and of sufficient depth to accommodate a number, preferably at least two, disposable syringe assemblies. Partition walls separate the slots from one another. These slots are labeled at the top or bottom, or both, with the days of a calendar week. These labels may be permanent and a part of the interior unit or tray, or may be self-adhesive tags or the like and arranged beginning with an individual's day of preference and continuing on in proper sequence.

These seven elongated slots are filled with an individual's choice of disposable syringe assemblies (syringe barrel, plunger, needle and protective caps at both ends), in order of requirements by day, i.e., one or more a day. Each day, on a prescribed schedule, a syringe assembly is removed from the slot labeled with the current day of the week. The syringe assembly is easily removable from its slot by means of a finger-tip receiving groove positioned about midway down the entire center length of the series of partition walls between the syringe slots. Persons with large hands or limited mobility can easily extract a single syringe assembly, as desired. After an injection, the spent syringe assembly may be rendered further unusable by placing the needle in the aperture of the needle breaking means and simply breaking off the needle, which is then automatically stored in the well area, while the rest of the syringe assembly is simply thrown away.

These and other objects, advantages, features, characteristics and further details of the invention will become more apparent to those skilled in the art by reference to the following description of preferred embodiments thereof, when taken in conjunction with the accompanying drawings, wherein like reference characters refer to like elements throughout the various views.

DETAILED DESCRIPTION OF PREFERRED EMBODIMENTS

Figure 1:
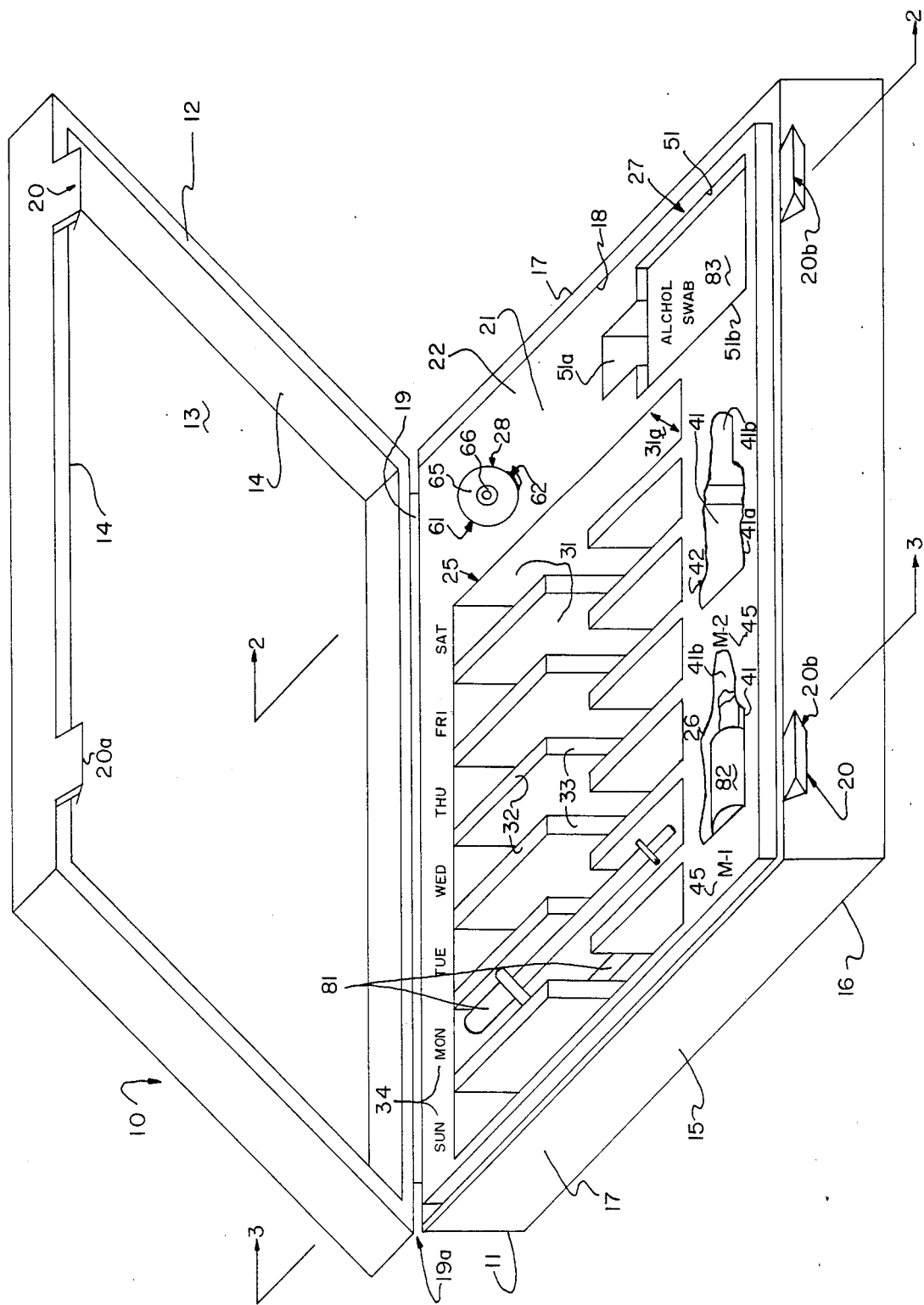
FIG. 1 is a somewhat isometric view of an embodiment of the injection monitor appliance of the invention, partially opened and partially filled with syringe assemblies, medication containers and alcohol swabs.

The invention provides an improved injection monitor appliance, device or kit enabling an insulin or injection-dependent person to positively and safely, at-a-glance, monitor daily injections.

The inventive device or kit maintains sufficient syringes, medication, alcohol swabs and a needle-disposal means in a relatively light-weight, sanitary, rugged, highly-portable, durable, nearly foolproof and economical appliance capable of storing or maintaining an individual's injection requirements for a select period of time, such as a full calendar week.

The inventive appliance includes a relatively rigid container assembly formed of upper and lower closure members. The container assembly is formed from a suitable material, such as plastic, for example polyvinyl chloride (PVC) or some other suitably durable material, such as aluminum. In certain embodiments, the container assembly may have any desired degree of clarity or, in other embodiments, a suitable clear window may be provided, for example, in the upper closure member, to enable a user to quickly take account of any interior contents. The container assembly is formed to be smooth, with no rough edges or the like to catch or abrade, inside and out. In an exemplary embodiment, the container assemble is provided with dimensions of about 30 cm (12 inches) in length, about 20 cm (8 inches) in width by about 6 cm (2½ inches) in height. Further, the container assembly of the exemplary embodiment is relatively lightweight, ranging from a a few grams (few ounces) to about 1 kilogram (about 2½ pounds).

The upper and lower closure members may be separate units adapted to selectively mate with one another along outer edges thereof so as to define a hollow space therebetween, which is sealable from external environment. In preferred embodiments, the closure members may be provided with a hinge means along adjacent side wall edges of each respective closure member so as to enable the closure members to selectively pivot toward and away from each other. A locking means, such as a snap-lock means or a series of mating ridges or lips embossed on a lateral side edge of respectively adjacent side walls of the closure members, opposite the hinge means, may be utilized to secure the closure members one to the other to define a unitary container assembly. It is important that the bottom wall of the upper closure member or lid of the container assembly, fit closely against the upper edge of the lower closure member or bottom of the container assembly, so that there is little or no chance for any accidental shifting of any contents within the hollow space in the container assembly. It is especially important and syringes or syringe assemblies stored in predetermined positions within the appliance are not accidentally interchanged or permanently moved out of their assigned positions, thereby negating the means for monitoring or tracking the injections administered or not. The closure member should securely mate with one another so that there is little chance for the appliance to unintentionally open, such as during transport or storage. As indicated earlier, embossed lips and/or ridges may be provided on respectively adjacent side wall edges of the closure members to provide a snap or pressure fit locking means. Other conventional lock closure means may also be utilized, if desired.

In certain embodiments, the lower closure member may be integrally formed with a tray therein, as by blow-molding, vacuum-forming or the like. In embodiments where a tray-receiving compartment is provided, a relatively semirigid tray is provided to securely fit within the tray-receiving compartment. The tray is formed of a suitable material, such as plastic, for example polyvinyl chloride or polystyrene or the like, which lends itself to the necessary forming steps, is durable, provides an easily cleanable or sanitizable surface, is somewhat deformable with a degree of memory or plasticity, and yet provides the desired degree of rigidity. The tray is formed with a number of slots, depressions, recesses and wells therein as will be explained hereinafter. The tray includes an upper wall plane, which, when the tray is positioned in the tray-receiving compartment of the container assembly, is substantially parallel with and generally abuts the bottom wall of the upper closure member when mated with the lower closure member so that there is a minimal clearance between the tray upper wall plane and the bottom wall of the upper closure member. The tray also includes a lower wall plane which, in proper position, is substantially parallel and abuts the bottom wall of the lower closure member.

The tray is provided with a plurality of parallely-disposed, horizontally-extending, open-topped elongated slots adapted to contain syringe assemblies therein. In preferred embodiments, the tray contains seven slots, one for each day of a calendar week. The slots are located in a first area on the tray so as to be readily accessible to a user. Each slot is designed to have a select depth and length dimension, with the depth dimension extending from the tray upper wall plane toward the lower wall plane. Preferably, each slot is adapted to contain a plurality (at least two) of typical disposable syringe assemblies (a 50 unit, 0.5 cc, syringe barrel or cylinder, plunger, needle and protractive caps at both ends). Preferably the slots are separated from each other by a partition wall, with a finger-tip receiving groove or opening located at a midpoint of each partition wall to enable a user to insert a finger-tip in a select groove and readily lift a syringe assembly therefrom. In an exemplary embodiment, the slots have approximate dimensions of about 2.54 cm (1 inch) in width by 13 cm (5 inches) in length by 2.54 cm (1 inch) in depth, with the groove in the partition wall being about 2.54 cm (1 inch) in width so that at least two syringe assemblies are readily stored in each slot and a user can lift a syringe assembly from such slot with a forefinger and thumb. The slots are labeled with an indicia means at their respective upper or lower (or both) ends, designating a select day of a week, enabling a user to quickly and accurately determine which slot (and syringe assembly) is to be utilized on a given day. The indicia may be permanently embossed or otherwise affixed to the upper wall area of the tray adjacent the slots. Further, the indicia may be placed on self-adhesive tags or labels which are then affixed adjacent a slot.

The tray is also provided with a plurality of medication-container receiving depressions at a second area of tray, adjacent and spaced from the first area thereof. In preferred embodiments, at least two (although more may be provided if desired) such depressions are provided. Each depression has outer dimension of about 2.54 cm (1 inch) in width by 7 cm (2¾ inches) in length by 2.54 cm (1 inch) in depth, with a somewhat tapered neck portion of about 2 cm (¾ inches) in length and a main portion area of about 2.2 cm (⅞ inches) in width. A medication bottle or container may be placed in such depression so that the front thereof is in the neck portion of the depression and a finger can be slipped in under the neck of the bottle or container and pried upwardly. Middle portions of the side walls of the main depression area, preferably extended inwardly to a certain degree so as to frictionally contact the medication container walls and securely hold the containers in place during transport of the monitor kit or appliance. In embodiments wherein two like depressions are provided, two different medications may be available in the kit, for example, in the case of a diabetic, regular and long acting insulin can be provided for use as necessary or desired. Indicia means may be associated with each depression to designate the type of medication in the container within each respective depression. The indicia means may be inscribed or affixed to the tray walls as desired.

The tray is also provided with a recess of a third area thereof, adjacent and spaced from the first and second areas. This recess is adapted to snugly receive a plurality (fourteen or more) of prewrapped alcohol swabs. The recess also has a main portion and a neck portion. In an exemplary embodiment, the recess is approximately 5.1 cm (2 inches) in width by 6.35 cm (2½ inches) in length by 3.3 cm (1 5/16) inches in depth, with the neck portion being about 2 cm (¾ inches) in length by 2.54 cm (1 inch) in width and a depth equal to the main portion. This neck portion allows a user to insert a finger tip and readily pick up an alcohol swab as desired.

A well opening is also provided on the tray at a fourth area thereof, adjacent and spaced from the other select areas thereof. The well opening is adapted to hold syringe needles after such needles have been broken off from the remaining syringe assemblies. The well opening has a generally circular periphery, with an approximate diameter of about 3.8 cm (1½ inches) and a depth of about 5.1 cm (2 inches). In certain embodiments, no separate bottom wall is required with the interior of the lower closure member of the overall assembly functioning as the bottom of the well opening.

A cover member is provided to frictionally fit (pressure fit) within the upper peripheral area of the well opening and seal off the bottom of the well opening from the top of the tray. The cover member is formed of a relatively rigid material, such as metal and is provided with a syringe-needle receiving aperture in a central area thereof. In an exemplary embodiment, the cover member is a stainless steel disc having a diameter of about 3.8 cm (1½ inches) and a thickness of about 0.64 cm (¼ inch), with a central aperture having a through hole diameter ranging from about 0.75 to about 0.25 millimeters. The aperture may be tapered from the upper face of the disc toward the lower face thereof, with the through hole diameter being at the lower face. A used needle, still attached to a syringe barrel, can thus be readily inserted into such aperture and the barrel moved back and forth sufficiently to break off the needle from the remaining syringe assembly. The broken off needle is safely stored in the well opening beneath the cover disc. A plurality of broken off needles can be so stored until it is convenient to more permanently dispose of the same. In certain embodiments, a tool-receiving depression may be provided along an upper peripheral area of the well opening for receiving a tool or tool edge for insertion beneath the cover member for selective removal thereof in emptying the well opening. After emptying the broken needles from the well opening, the cover member is again frictionally fitted within the upper peripheral area of the well opening and the device utilized as before. In embodiments where the overall container assembly and tray are manufactured as a single unit, a relatively large space is available beneath the lower wall plane of the tray and the bottom wall of the lower closure member for storage of broken off needles. When this space becomes filled with broken needles, the cover member may be removed and the overall assembly (after removal of any syringe assemblies, medication containers and/or alcohol swabs) turned upside down so that the broken off needles fall out of the well opening into a garbage can or other suitable disposal means.

Referring now to the drawings, an exemplary embodiment of the invention is illustrated but it will be understood that the invention is not limited to the exemplary embodiment shown and various changes and modifications can be made by those skilled in the art without departing from the spirit and scope of the invention.

At FIG. 1, the inventive assembly, device of kit 10 is illustrated and includes a rigid container assembly 11. The assembly 11 may be formed of any desired durable, lightweight, rigid, sanitizable material, such as an extruded plastic or aluminum. As indicated earlier, the container assembly 11 is preferably formed of polyvinyl chloride, although other suitable materials may be utilized. The container assembly 11 includes an upper closure member 12 having a bottom wall 13 and side walls 14 joined together to form a unit. The assembly 11 also includes a lower closure member 15 having a bottom wall 16 and side walls 17 joined together to form a unit. In certain embodiments, (best seen at FIGS. 2 and 3) the side wall 17 of the lower closure member is provided with a horizontal flange 17a for supporting a tray edge, as will be explained hereinafter. The respective bottom and side walls of the closure members 12 and 15 join together to form separate units, with at least the lower closure member having a tray-receiving compartment 18 therein.

In the embodiment illustrated, a hinge means 19 is provided along adjacent lateral side edges of the closure members 12 and 15 allowing the members to be selectively pivoted toward and away from one another. For ease of operation, a cut-out area 19a may be provided along both outer edges of the hinge means 19. The hinge means 19 may comprise a continuous strip of flexible material such as plastic, joined to respectively adjacent edges of the closure member 12 and 15 or may be a conventional piano hinge or the like secured to adjacent edges of the closure members. A locking means 20 may be provided on adjacent lateral side edges of the closure members, opposite the hinge means 19. The locking means 20 may comprise relatively flexible finger-like projections 20a adapted for cooperation with protruding ridges or lips 20b. The projections 20a are located along a free edge of a wall of one of the closure members 12 or 15 while the mating ridges 20b are located along a corresponding free edge of a cooperating wall of the other closure member. Other locking means may also be utilized if desired.

A semirigid tray 21 is provided to securely fit within the tray-receiving compartment 18 of lower closure member 15. The tray 21 includes an upper wall plane 22 and a lower wall plane 23 spaced therefrom. The rigidity of the tray is controllable by proper selection of material and material thickness. In the exemplary embodiment, the thickness of the tray walls is in the range of about 0.03 cm to about 0.3 cm, (0.012 to 0.120 inches). The tray 21 is formed of a suitable material having sufficient rigidity to withstand normal everyday use and yet be relatively pliable with sufficient resiliency or memory to allow select portions or compartments thereof to be momentarily deformed or the like so as to hold, as by compression, articles placed within recesses or compartments provided on the tray. In an exemplary embodiment, the tray 21 is formed of polystyrene or similar thermoplastic material which has the desired rigidity and resiliency and can be readily cleansed or sanitized as required.

Figure 2:
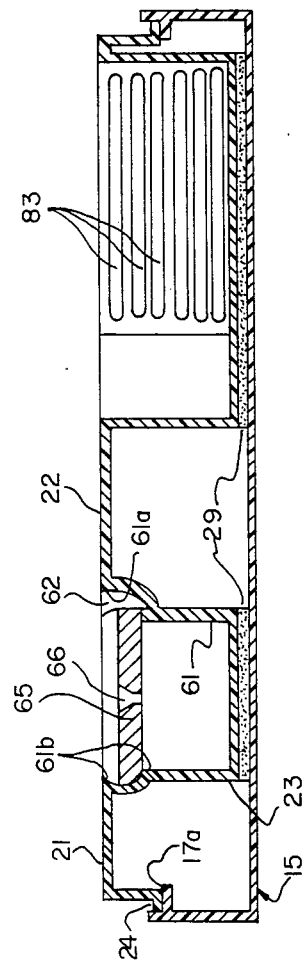
FIG. 2 is a cross-sectioned view taken substantially along lines 2—2 of FIG. 1.
Figure 3:
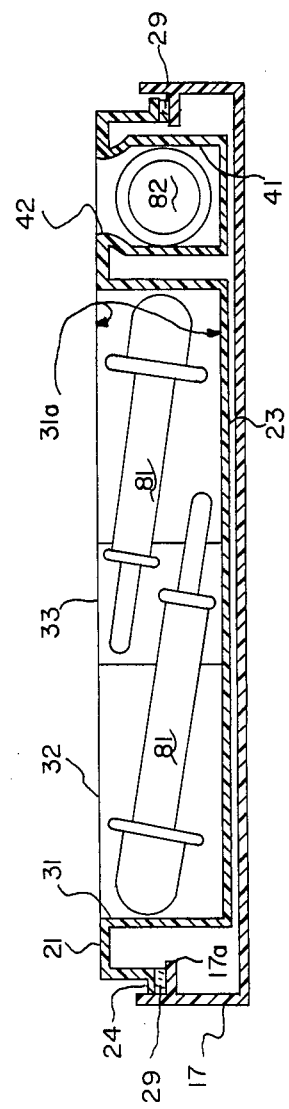
FIG. 3 is a cross-sectioned view taken substantially along lines 3—3 of FIG. 1.

The upper wall plane 22 of tray 21 is formed to be high enough so that when the upper closure member 12 is moved downwardly to mate or lock with the lower closure member 15, there is a slight compression or minimal clearance between the top surface of the upper wall plane 22 of tray 21 and the inside bottom of upper closure member 12. This minimal clearance prevents syringe assemblies and alcohol swabs from moving beyond their respectively assigned positions or compartments in the tray 21. It is especially important to insure that no accidental movement of syringe assemblies takes place since injection monitoring or tracking is dependent on the relationship between the syringe assemblies and the indicia (typically days of a calendar week) associated with the slots in the tray In certain embodiments, the tray 21 may include a lateral side wall edge 24 (FIGS. 2 and 3) for cooperation with the horizontal flange 17a of the lower closure member side wall 17. In some embodiments, the tray 21 is formed of a size to fit snugly within the tray-receiving compartment 18 so that the lateral side walls thereof abut and are somewhat biased against corresponding side walls 17 of the lower closure member. In other embodiments an adhesive layer or coating 29 is provided either along the adjacent lateral side walls, as shown in FIG. 3, or along select areas of the bottom face of the lower wall plane 23, as shown in FIG. 2. Yet, in other embodiments, the tray and lower closure members are formed as an integral unit.

Figure 6:
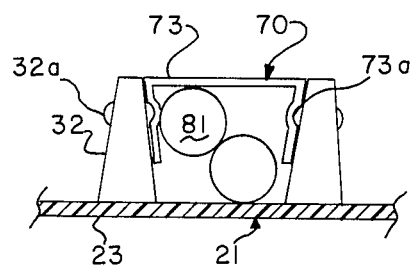
FIG. 6 is an elevated cross-sectional and fragmentary view similar to that shown in FIGS. 4 and 5 of yet another embodiment of a retaining means of the invention.

The tray 21 includes spaced apart areas, such as a first area 25, a second area 26, a third area 27 and a fourth area 28, containing slots 31, depressions 41, a recesses 51 and a well opening 61. The first area 25 is, in the embodiment shown, located at the upper left hand corner of tray 21 and is provided with a plurality of slots 31. As shown, slots 31 are parallelydisposed, extend horizontally and are open-topped to allow ready access to the interiors thereof. Each slot 31 has a depth dimension 31a adapted to accommodate a select number of syringe assemblies 81 therein. Preferably, each slot can accommodate two syringe assemblies positioned as shown at FIG. 3. The slots 31 are of a length sufficient to accommodate standard size syringe assemblies and are separated from each other by respective partition walls 32. In certain embodiments, such as shown at FIG. 6, wall protuberances 32a may be provided as an aid in maintaining syringe assemblies within a given groove. The partition walls 32 are each provided as an aid in maintaining syringe assemblies within a given groove. The partition walls 32 are each provided with a fingertip receiving open groove 33 located at about the midpoint area of each wall. The open groove 33 allows a user to easily grasp a syringe assembly within a given slot 31.

A first indicia means 34 is associated with each slot, either along the top thereof as shown or, alternatively, along the bottom (although if desired, the indicia may be provided along the top and bottom). The indicia means preferably comprises the names of a given day in a standard calendar week although nonstandard weeks, such as beginning on, for example, Friday and extending to the next Friday, may be utilized. Further, numerical representations may be utilized if desired.

The second area 26 of the tray is, in the embodiment shown, located below and in front of the first area 25. Area 26, in the embodiment shown, is provided with two medication container-receiving depressions 41. The depressions 41 are open-topped and extend laterally and generally parallel to the side walls of the lower closure member 15. Each depression includes a main cavity area 41a and a neck cavity area 41b joined together. The peripheral side walls of each main cavity area 41a may be provided with inwardly extending ridges or protuberances 42, preferably along the upper peripheral edge of the depressions, to aid in snugly retaining, as by friction, the medication containers or bottles 82 placed therein. Typical medication containers or bottles for use by injection-dependent persons are relatively standard in size so that various insulin medications or other injection-type medications can be readily stored in such containers and the containers pushed past the inwardly extending ridges 42. Once a medication container 82 is within a depression 41, the containers 82 is securely held in position and cannot come out unless it is forced out by upward pressure. Thus, when one desires to remove a medication container 82 from a depression 41, a fingertip or the like is inserted into the neck portion 41b of the depression and placed beneath the neck of the container and pulled upwardly so that the container stands upright in the depression. The container can then be easily removed for use as desired.

In embodiments where a diabetic is utilizing the invention, the two depressions allow regular insulin and long acting insulin to be readily transported for use in the inventive appliance.

A second indicia means 45 may be associated with each depression 41. The second indicia preferably comprises the names of a given medication, although numerical or other designations may also be utilized. The second indicia may be permanently affixed or inscribed within the upper wall of tray 21 adjacent each depression. Alternatively the desired indicia may be provided on tags or labels having an adhesive coating thereon allowing securement thereof onto the tray wall.

The third area 27 of the tray 21 is, in the embodiment shown, located to the right of the second area 26 and somewhat below the first area 25. Area 27 is provided with a prewrapped alcohol swabs receiving recesses 51. Standardized commercial prewrapped alcohol swabs 83 are readily available and are used by injection dependent persons to sterilize a skin area and/or medication container opening prior to administering an injection. Recesses 51 is formed to have a neck portion 51a and a main cavity or pocket portion 51b. The neck portion is of a size to readily accommodate a finger tip of a person and facilitates the ready removal of a prewrapped alcohol swab when desired. The main cavity portions 51b is of a size to snugly receive a plurality of relatively standardized prewrapped alcohol swabs 83. Typically, the recesses 51 is of a size to readily accommodate at least fourteen swabs and may accommodate more.

The fourth area 28 of tray 21 is, in the embodiment shown, located above the third area and generally to the right of the first area 25. Area 28 is provided with a well opening 61 (best seen at FIG. 2) having a select diameter and extending from the upper wall plane 22 downwardly at least to the bottom wall plane 23 of tray 21. The upper peripheral area 61a of the opening 61 is shaped to define a somewhat concave step or ridge 61b and is provided with a tool receiving depression 62 at a select region of upper peripheral area 61a. The concave ridge 61a snugly supports a cover member or disc 65 over the open top of opening 61. The resiliency of the material forming the tray allows the disc 65 to be pressure fitted into the concave ridge 61a and retained therein until removed by a tool inserted into depression 62. The cover member 65 is provided with a needle-receiving aperture 66 at a central area thereof. As shown at FIG. 2, the aperture may be tapered inwardly to readily accommodate a standard syringe needle. The tapered slope of the aperture 66 allows a user to more easily find the aperture with a needle point and insert the same therein. The through hole diameter at the bottom of the aperture 61 confines the syringe needle to a very limited space so that when an attached syringe barrel is moved back and forth above the aperture, the needle breaks off from the barrel and falls into the cavity of opening 61. The legitimate user of the syringe assembly is then assured to no improper use of the spent syringe assembly will occur. After the well opening 61 is filled or at least partially filled with broken off needles, the cover member 65 may be removed with the aid of a tool or tool edge and the broken off needles safely disposed. The cover or disc 65 is then snapped back into position for further use.

In order to further insure against acridental movement of syringe assemblies from their assigned slots, retaining means 70 may be provided in working relationship with each slot to securely maintain a select number of syringe assemblies within such slot.

Figure 4:
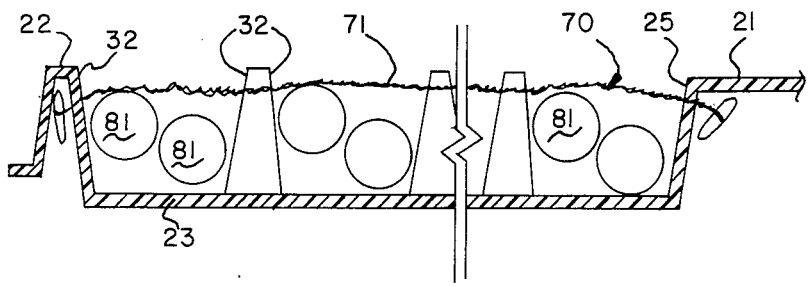
FIG. 4 is an elevated cross-section and fragmentary view, partially schematic and partially broken away, illustrating an embodiment of a retaining means of the invention.

FIG. 4 illustrates a retaining means 70 which comprises an elastomeric band 71 extending across each respective slot, preferably at an area coinciding with the open groove 33 in the partition walls 32. The ends of the elastomeric band 71 may be suitably anchored at least at the outermost portions of the upper edges of the partition walls, as shown.

Figure 5:
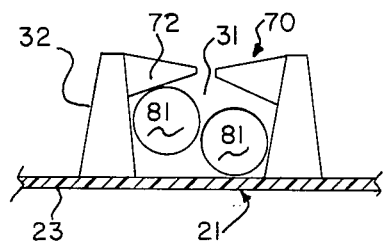
FIG. 5 is an elevated cross-sectional and fragmentary view similar to that shown at FIG. 4 of another embodiment of a retaining means of the invention.

FIG. 5 illustrates another embodiment of retaining means 70, which comprises deformable lips 72 attached to the side walls of each partition wall 32 so as to extend inwardly across each slot 31. The lips 72 may be formed of a synthetic foam, such as a closed or open cell polyurethane foam. Of course other suitable materials may also be utilized.

FIG. 6 illustrates yet another embodiment of retaining means 70, which comprises a snap-lock cap 73 which frictionally fits between adjacent partition walls 32. In some forms of this embodiment, the partition walls 32 may be provided with wall protuberances 32a and the snap-lock caps may be provided with corresponding recesses 73a to cooperate with the protuberances 32a and securely hold syringe assemblies 81 is place.

We claim:
1. A relatively safe, foolproof, light-weight, portable, durable and economical injection monitoring appliance adapted for use by injection-dependent individuals to maintain a daily monitoring of injections taken, comprising, in combination:

a relatively rigid container assembly having an upper closure member and a lower closure member, each respective member having bottom and side walls joined together and each member adapted to mate with the other to define a hollow space therebetween selectively sealable from external environment;

at least said lower closure member having a tray-receiving compartment therein;

a relatively semirigid tray adapted to securely fit within said tray-receiving compartment, said tray having an upper wall plane substantially parallel with and abutting with said bottom wall of said upper closure member when mated with said lower closure member with a minimal clearance between said tray upper wall plane and said bottom wall of the upper closure member;

a plurality of parallely-disposed, horizontally-extending, open-topped elongated slots located at a first area on said tray, each of said slots having a depth dimension extending from said tray upper wall plane toward a lower wall plane thereof and adapted to contain a select number of syringe assemblies therein, said slots being separated from each other by respective partition walls with a finger-tip receiving open groove located at a midpoint area of each partition wall;

first indicia means associated with each respective slots designating a select day of a week thereon;

a plurality of medication container-receiving depressions located on said tray at a second area thereof adjacent and spaced from said first area;

second indicia means associated with each respective depression designated a type of medication in the container within such depression;

a recess located on said tray at a third area thereof adjacent and spaced from said first and second areas thereof for snugly receiving a plurality of prewrapped alcohol swabs therein;

a well opening located on said tray at a fourth area thereof adjacent and spaced from said first, second and third areas thereof for receiving syringe needles therein; and a cover member frictionally fitting within an upper peripheral area of said well opening, said cover member having a syringe-needle receiving aperture in a central area thereof to aid in breaking off needles from spent syringe assemblies.

2. An injection monitoring assembly as defined in claim 1 wherein said upper and lower closure members are joined to one another along select adjacent lateral side edges thereof by a hinge means allowing said members to be selectively pivotable toward and away from each other, said members having a locking means located on adjacent lateral side edges thereof opposite said hinge means.

3. An injection monitoring assembly as defined in claim 1 wherein said semirigid tray is adhesively secured to the bottom wall of said lower closure member.

4. An injection monitoring assembly as defined in claim 1 whereas said semirigid tray is an integral portion of said lower closure member.

5. An injection monitoring assembly as defined in claim 1 wherein the plurality of elongated slots consists of at least seven slots, each associated with indicia designating a respective day of a calendar week.

6. An injection monitoring assembly as defined in claim 1 wherein said cover member is metallic body having an aperture with a through hole diameter ranging from about 0.75 to about 0.25 mm.

7. An injection monitoring assembly as defined in claim 1 wherein said well opening includes a tool-receiving depression along the upper peripheral area of said opening allowing a tool to be inserted beneath the cover member for selective removal thereof.

8. An injection monitoring assembly as defined in claim 7 wherein said well opening is of a depth sufficient to accommodate a plurality of syringe needles.

9. An injection monitoring assembly as defined in claim 1 wherein retaining means are provided in working relation with each respective slot to securely maintain a select number of syringe assemblies within such slot.

10. An injection monitoring assembly as defined in claim 9 wherein said retaining means comprises an elastomeric band extending across each respective slot, with ends of said band being anchored at least at the outermost portions of upper edges of said partition walls.

11. An injection monitoring assembly as defined in claim 9 wherein said retaining means comprises deformable lips attached to a side wall of each partition wall and extending toward one another across each respective slot.

12. An injection monitoring assembly as defined in claim 9 wherein said retaining means comprises a snap-lock cap frictionally fitting between adjacent partition walls and across each respective slot.

13. An injection monitoring assembly as defined in claim 1 wherein said lower closure members include horizontal flanges located below upper edges of the side walls thereof and extending inwardly to define first support surfaces; and said tray includes horizontal shoulders located below said tray upper wall plane and extending outwardly to define second support surfaces, said first and second support surfaces overlying and abutting one on the other.

14. A relatively safe, foolproof, light-weight, portable, durable and economical injection monitoring appliance adapted for use by injection-dependent individuals to maintain a daily monitoring of injections taken, comprising, in combination:

A relatively rigid container assembly having an upper closure member and a lower closure member, each respective member having bottom and side walls joined together and each member adapted to mate with the other to define a hollow space therebetween selectively sealable from external environment, said upper and lower closure members being joined to one another along select adjacent lateral side edges thereof by a hinge means allowing said members to be selectively pivotable toward and away from each other, said closure member having a locking means located on adjacent lateral side edges thereof opposite said hinge means;

at least said lower closure member having a tray-receiving compartment therein;

a relatively semirigid tray securely affixed within said tray-receiving compartment, said tray having an upper wall plane substantially parallel with and abutting with said bottom wall of said upper closure member when mated with said lower closure member with a minimal clearance between said tray upper wall plane and said bottom wall of the upper closure member;

a plurality of parallely-disposed, horizontally-extending, open-topped elongated slots located at a first area on said tray, each of said slots having a depth dimension extending from said tray upper wall plane toward a lower wall plane thereof and adapted to contain a select number of syringe assemblies therein, said slots being separated from each other by respective partition walls with a finger-tip receiving open groove located at a midpoint area of each partition wall;

first indicia means associated with each respective slots designating a select day of a week thereon;

a plurality of medication container-receiving depressions located on said tray at a second area thereof adjacent and spaced from said first area;

second indicia means associated with each respective depression designated a type of medication in the container within such depression;

a recess located on said tray at a third area thereof adjacent and spaced from said first and second areas thereof for snugly receiving a plurality of prewrapped alcohol swabs therein;

a well opening located on said tray at a fourth area thereof adjacent and spaced from said first, second and third areas thereof for receiving syringe needles, said well opening including a tool receiving depression along the upper peripheral area of said opening allowing a tool to be inserted therein for selective removal of a cover member in said opening; and a metal cover member frictionally fitting within an upper peripheral area of said well opening, said cover member having a syringe-needle receiving aperture in a central area thereof to aid in breaking off needles from spent syringe assemblies, said aperture having a through hole diameter ranging from about 0.75 to about 0.25 mm.

* * * * *